(12) United States Patent
Sakata et al.

(10) Patent No.: US 6,477,409 B2
(45) Date of Patent: Nov. 5, 2002

(54) APPARATUS FOR MEASURING BASAL METABOLISM

(75) Inventors: Kazuhiko Sakata, Saitama; Miyuki Kodama, Tokyo; Hitoshi Sato, Tsurugashima, all of (JP); Steven B. Heymsfield, Mount Kisco, NY (US)

(73) Assignee: Tanita Corporation, Tokyo (JP)

( * ) Notice: Subject to any disclaimer, the term of this patent is extended or adjusted under 35 U.S.C. 154(b) by 0 days.

(21) Appl. No.: 09/920,297

(22) Filed: Aug. 2, 2001

(65) Prior Publication Data

US 2002/0040197 A1 Apr. 4, 2002

Related U.S. Application Data

(60) Provisional application No. 60/237,402, filed on Oct. 4, 2000.

(51) Int. Cl.[7] .................................................. A61B 5/00
(52) U.S. Cl. ........................................................ 600/547
(58) Field of Search ................................. 600/300, 547, 600/587

(56) References Cited

U.S. PATENT DOCUMENTS

| | | | | |
|---|---|---|---|---|
| 5,415,176 A | * | 5/1995 | Sato et al. | 600/547 |
| 5,611,351 A | * | 3/1997 | Sato et al. | 600/547 |
| 6,088,615 A | * | 7/2000 | Masuo | 600/547 |
| 6,198,964 B1 | * | 3/2001 | Oguma | 600/547 |
| 6,256,532 B1 | * | 7/2001 | Cha | 600/547 |

* cited by examiner

*Primary Examiner*—Max Hindenburg
(74) *Attorney, Agent, or Firm*—McDermott, Will & Emery

(57) ABSTRACT

An apparatus for measuring basal metabolism includes a device to input individual data, for example an age of a subject; a device to measure bioelectrical impedance of the subject; a device for calculation of fat-free mass on the basis of the individual data and the impedance;, and a device for calculation of basal metabolism of the subject on the basis of a reciprocal of the age and the fat-free mass. The basal metabolism can be calculated using the formula represented by BMR=A×FFM+B×(1/age)+C, in which BMR is basal metabolism (kcal/day), FFM is fat-free mass (kg), and A, B, and C are constants.

9 Claims, 18 Drawing Sheets

MOUNT PLATFORM TO MEASURE YOUR BODY WEIGHT

YOUR BODY WEIGHT IS 75.0kg

FIG. 18

| HEIGHT | 170cm | BODY WEIGHT | 70.0kg |
| AGE | 50YEARS | BODY FAT RATE | 23.0% |
| BASAL METABOLISM | | 1,531kcal/DAY | |
| TOTAL AMOUNT OF CONSUMPTION ENERGY | | 2,296kcal/DAY | |

BODY WITH TENDENCY TO BE FAT   STANDARD   BODY WITH TENDENCY NOT TO BE FAT

FIG. 19

INPUT YOUR HEIGHT.
THEN, PUSH SET KEY.

160.0cm

APPARATUS FOR MEASURING BASAL METABOLISM

RELATED APPLICATIONS

This application claims priority from U.S. Provisional Patent Application Ser. No. 60/237,402, filed Oct. 4, 2000.

FIELD OF THE INVENTION

The present invention relates to determining basal metabolism of a patient, and more particularly, to an apparatus for measuring basal metabolism using fat-free mass.

BACKGROUND OF THE INVENTION

Expensive and extensive apparatus are usually necessary to determine accurate basal metabolism of a subject. Additionally, many loads and measuring conditions are required, and a subject has to keep at rest for a long time with wearing a facemask and a mouthpiece. In addition, only a specialist can handle the measuring apparatus and evaluate the measured results. As such, the general public can hardly perform their own tests to obtain an accurate measure of their own basal metabolism.

For these reasons, a statistically standard basal metabolism value is used in most cases to determine basal metabolism. The statistically standard basal metabolism value is obtained, for example in Japan, by multiplying a reference value of basal metabolism on the basis of gender and age according to Health Service Bureau of Ministry of Health and Welfare by body weight. This standard value is used despite the importance of a relationship between adiposis and basal metabolism.

Basal metabolism, however, is considered to be directly proportional to fat-free mass rather than to actual body weight. As shown in FIG. 1, the basal metabolism determined using the above-mentioned method is suitable for a human having a standard body build and a standard body composition, because body composition is a strong effective factor. However, a calculated value of basal metabolism tends to be higher than an observed value of basal metabolism in a pycnic type (i.e., a human with a high fat rate) who has a heavy body weight and a large amount of fat. Also, a calculated value of basal metabolism tends to be lower than an observed value of basal metabolism in a slim and muscular man (i.e., a human with a low fat rate). Therefore, the above-mentioned method for calculating basal metabolism is not preferable from the viewpoint of guidance for adiposis.

Since basal metabolism has a close relation to the fat-free mass, a formula represented as follows is employed in a foreign nutrition science academy.

$$BMR = A \times FFM + B$$

BMR is basal metabolism (kcal/day), FFM is fat-free mass (kg), and A and B are constants. The relationship between the basal metabolism and the fat-free mass is shown in FIG. 2. This formula produces a correlation coefficient of 0.824, which shows the formula closely correlates with observed results. However, the basal metabolism obtained with the above mentioned formula is adapted to adults but not to children in a growth period. In addition, the calculated value with the formula tends to be lower than an observed value in a person having a low fat-free mass, especially in young slim females according to the measured results by the present inventors. Accordingly, a need exists for an improved apparatus for calculating basal metabolism that provides a calculated value that more accurately correlates with the observed value of basal metabolism so that guidance can be effectively provided as to diet and exercise for a pycnic type person and also to children.

SUMMARY OF THE INVENTION

These and other needs are met by embodiments of the present invention which provide an apparatus for measuring basal metabolism. The apparatus includes a device to input individual data, for example an age of a subject; a device to measure bioelectrical impedance of the subject; a device for calculation of fat-free mass on the basis of the individual data and the impedance; and a device for calculation of basal metabolism of the subject on the basis of a reciprocal of the age and the fat-free mass. By adding the reciprocal of an age as a factor in determining basal metabolism, in addition to fat-free mass, the present invention improves the accuracy of an arithmetic method used to determine basal metabolism.

In an aspect of the present invention, basal metabolism can be determined using the formula represented by $BMR = A \times FFM + B \times (1/age) + C$, in which BMR is basal metabolism (kcal/day), FFM is fat-free mass (kg), and A, B, and C are constants.

In accordance with another aspect of the present invention, the device can determine basal metabolism using the formula represented by $BMR = A \times FFM^2 + B \times FFM + C \times (1/age) + D$, in which BMR is basal metabolism (kcal/day), FFM is fat-free mass (kg), and A, B, C, and D are constants.

In an additional embodiment, the invention includes a device to input individual data, for example age and body weight of a subject; a device to measure bioelectrical impedance of the subject; a device for calculation of fat-free mass on the basis of a reciprocal of the individual data and the impedance; and a device for calculation of basal metabolism of the subject on the basis of the age, the body weight, and the fat-free mass. By adding both age and weight as factors in determining basal metabolism, in addition to fat-free mass, the present invention improves the accuracy of an arithmetic method used to determine basal metabolism.

In an aspect of the invention, the basal metabolism can be determined using the formula represented by $BMR = A \times FFM + B \times (1/age) + C \times body\ weight + D$, in which BMR is basal metabolism (kcal/day), FFM is fat-free mass (kg), and A, B, C, and D are constants.

In another aspect of the invention, the basal metabolism is calculated with a formula represented by $BMR = A \times FFM^2 + B \times FFM + C \times (1/age) + D \times body\ weight + E$, in which BMR is basal metabolism (kcal/day), FFM is fat-free mass (kg), and A, B, C, D, and E are constants.

In other aspects of the invention, the present invention is a portable apparatus without a weighing machine in which the subject's body weight is manually inputted into the input device. Alternatively, the subject's body weight can be inputted as a signal from a device that measures body weight. Still further, the body fat measuring assembly can be attached to a weighing machine and the subject's body weight can be inputted as a signal simultaneously to when the impedance is measured.

Additional advantages of the present invention will become readily apparent to those skilled in this art from the following detailed description, wherein only the preferred embodiment of the present invention is shown and described, simply by way of illustration of the best mode contemplated for carrying out the present invention. As will be realized, the present invention is capable of other and different embodiments, and its several details are capable of modifications in various obvious respects, all without departing from the invention. Accordingly, the drawings and description are to be regarded as illustrative in nature, and not as restrictive.

BRIEF DESCRIPTION OF THE DRAWINGS

Reference is made to the attached drawings, wherein elements having the same reference numeral designations represent like elements throughout, and wherein:

FIGS. 14 to 22 are examples of displays on a display portion in accordance with the present invention.

DETAILED DESCRIPTION OF THE INVENTION

Figure 3:
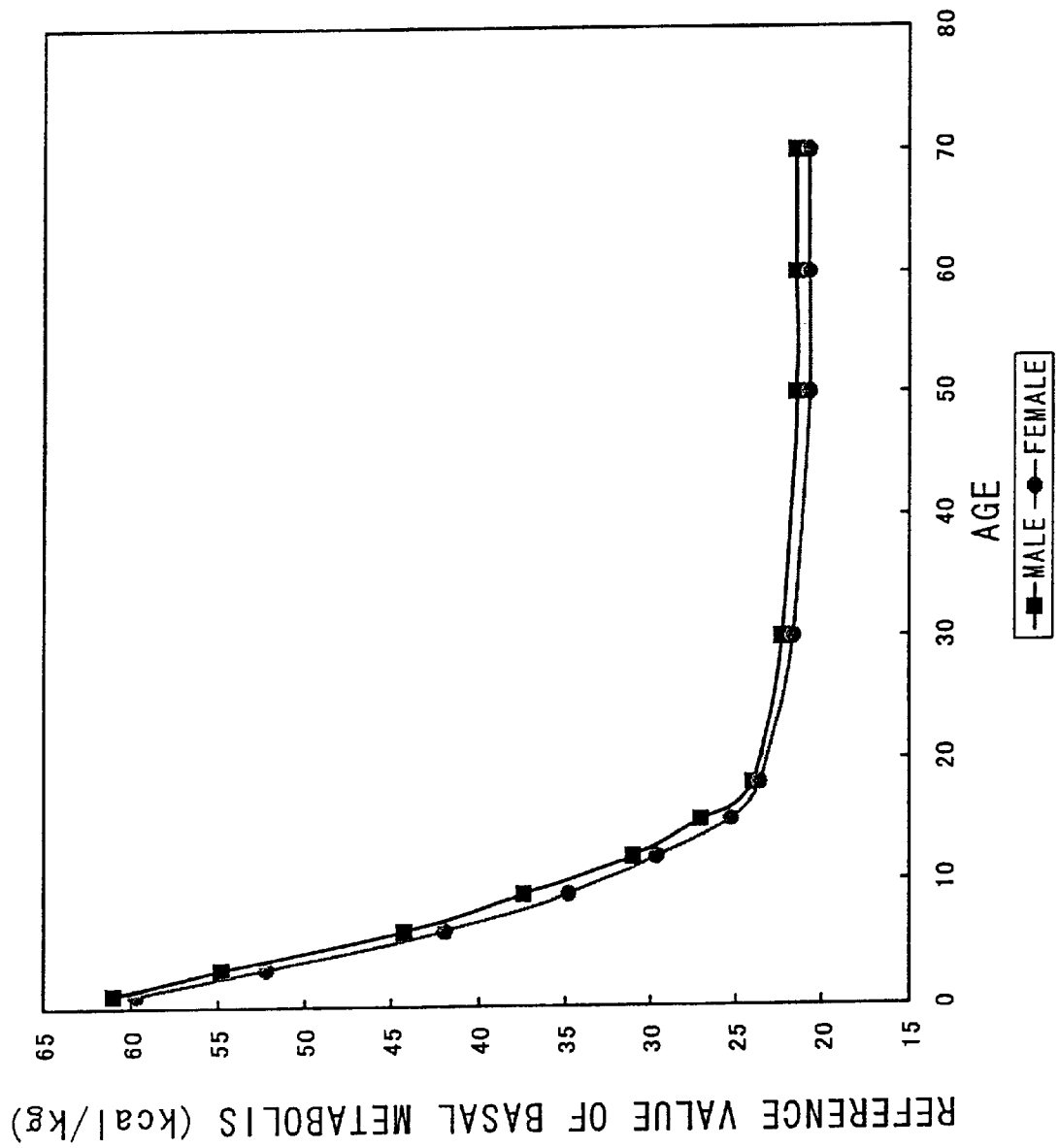
FIG. 3 is a graph showing a relationship between an age and a reference value of basal metabolism.
Figure 4:
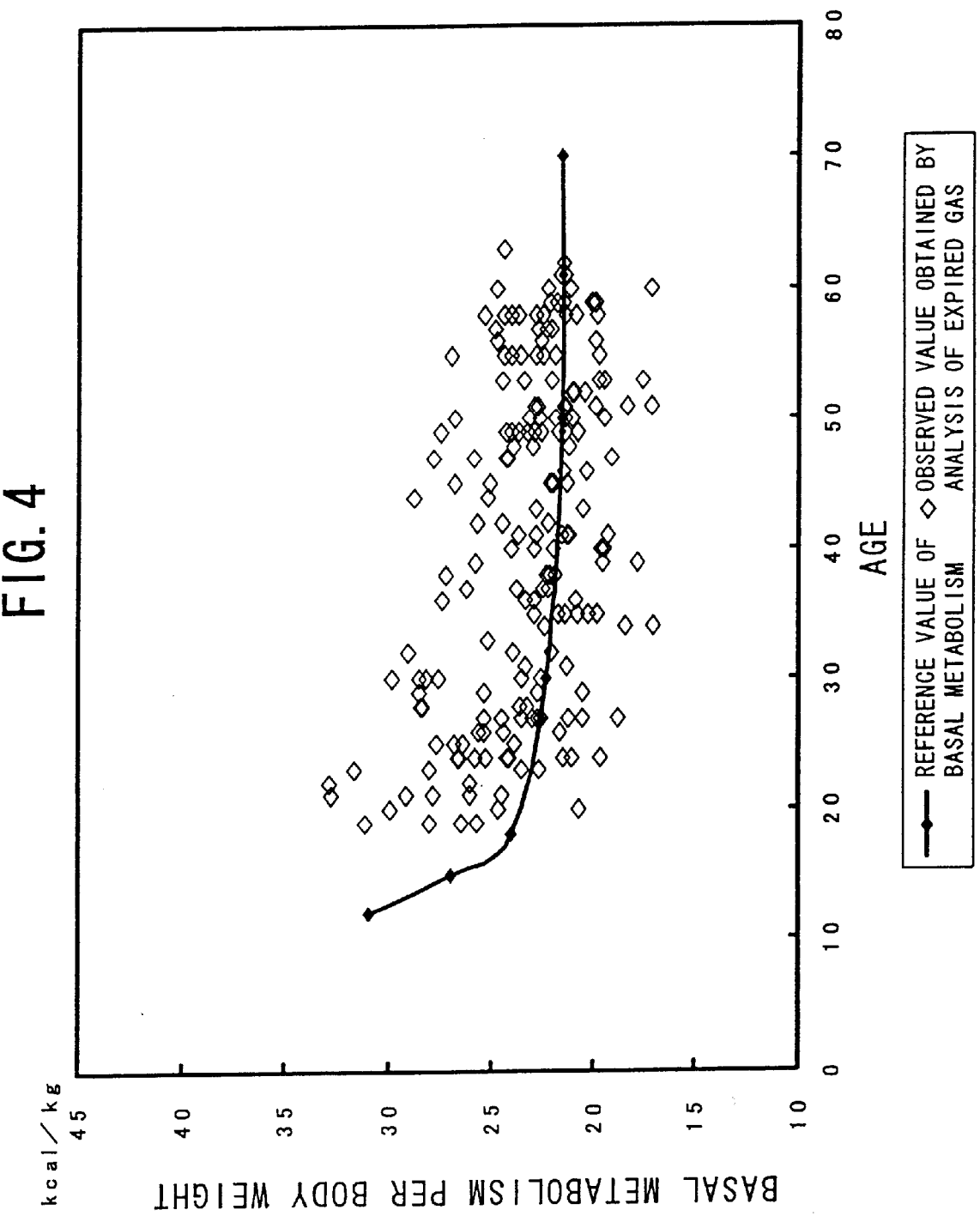
FIG. 4 is a graph showing a relationship between basal metabolism per body weight and an age.

An embodiment of the present invention will be described with reference to the figures. As shown in FIG. 3, the inventors of the present invention have reviewed the values of basal metabolism provided by the Health Service Bureau of Ministry of Health and Welfare and have determined that these values are inversely proportional to age of the subject. In addition, as illustrated in FIG. 4, the inventors of the present invention have independently observed that basal metabolism per body weight is inversely proportional to an age. Furthermore, the inventors have of the present invention have found that a reciprocal of an age in addition to fat-free mass is preferably utilized when calculating basal metabolism. Accordingly, the inventors have found that the basal metabolism can be calculated using the formula represented by BMR=A×FFM+B×(1/age)+C, in which BMR is basal metabolism (kcal/day), FFM is fat-free mass (kg), and A, B, and C are constants. It should be understood, however, that the formula is not limited to using metric measuring system values and can use any type of measuring system values.

Figure 5:
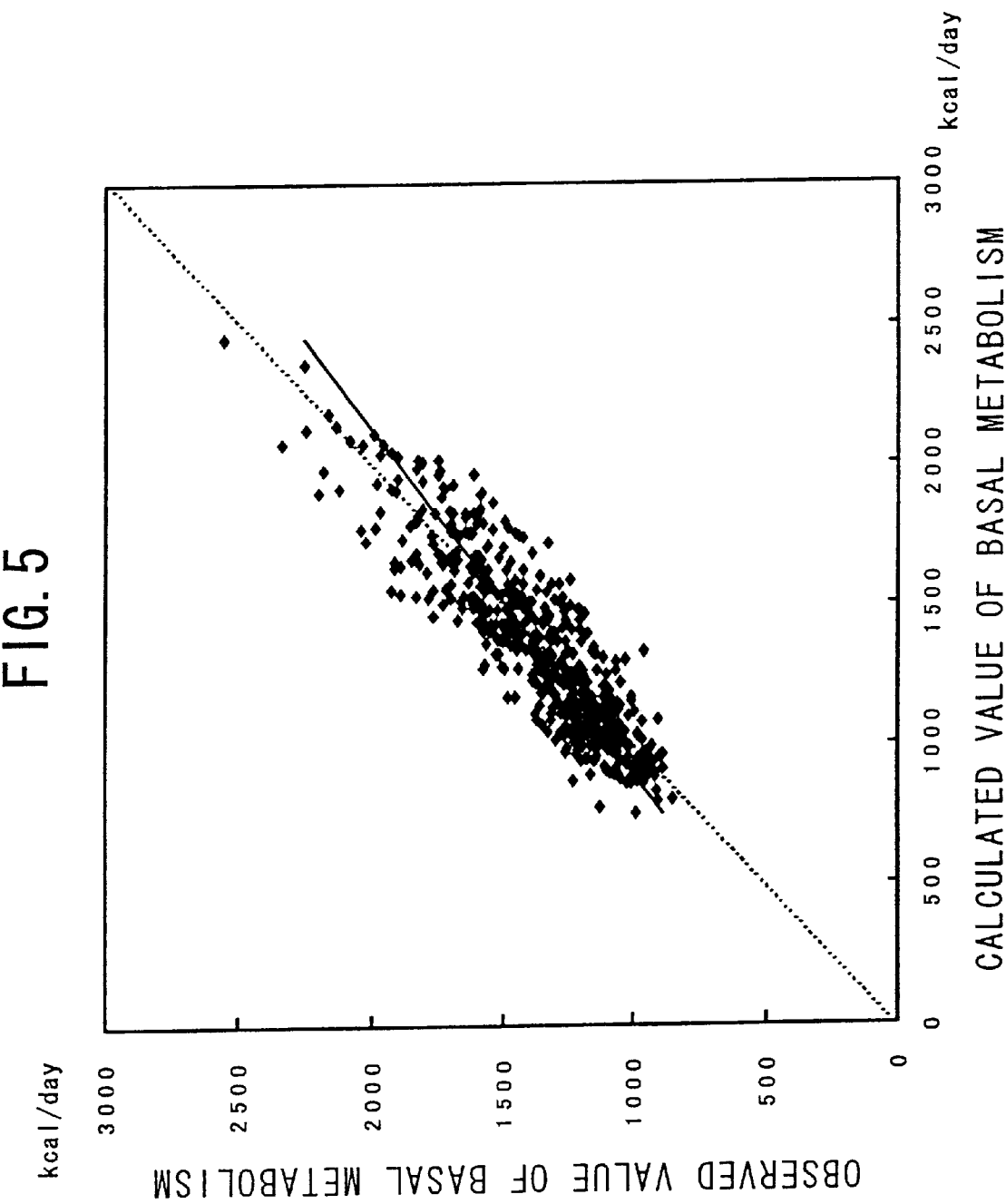
FIG. 5 is a graph showing a relationship between a calculated value of basal metabolism and an observed value of basal metabolism.
Figure 6:
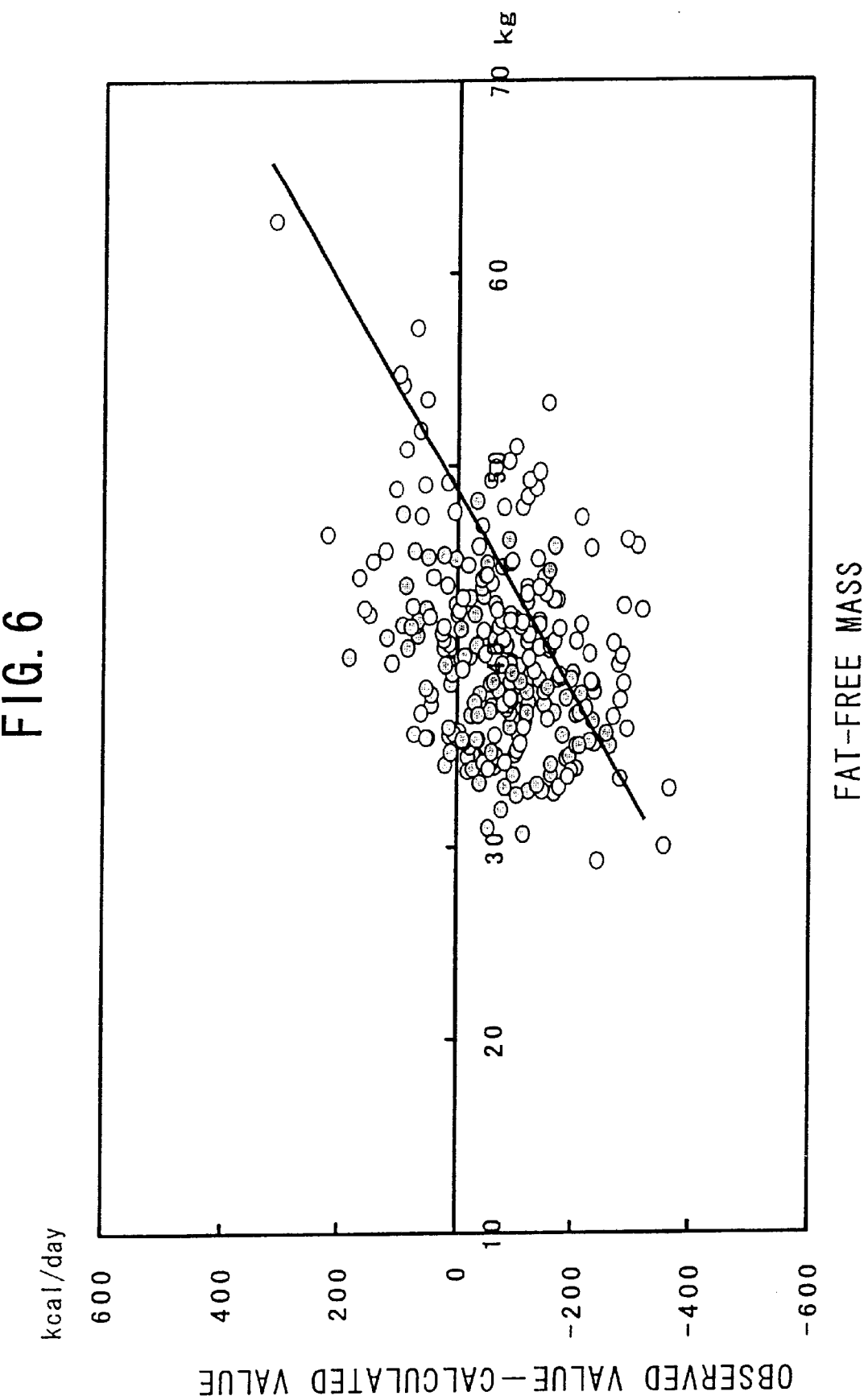
FIG. 6 is a graph showing a relationship between difference between an observed value of basal metabolism and a calculated value of basal metabolism and fat-free mass.

As shown in FIG. 5, a correlation coefficient between the basal metabolism obtained using the above mentioned formula and the observed basal metabolism is 0.870. The observed value was obtained by analysis of expired gas. As shown in FIG. 6, the difference between an observed value and a calculated value against fat-free mass is half of the conventional data.

Figure 1:
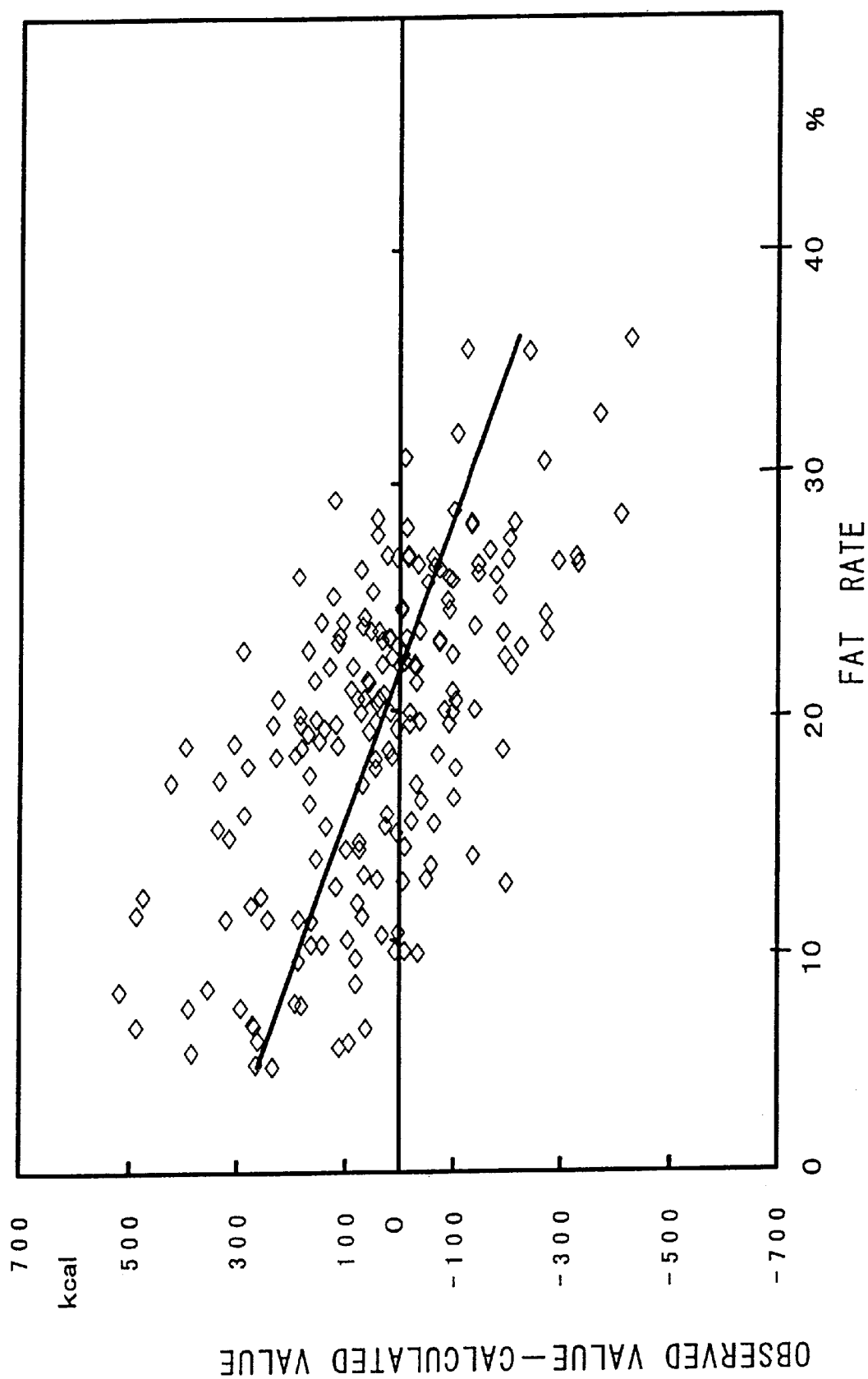
FIG. 1 is a graph showing a relationship between difference between an observed value of basal metabolism and a calculated value of basal metabolism and a fat rate.
Figure 2:
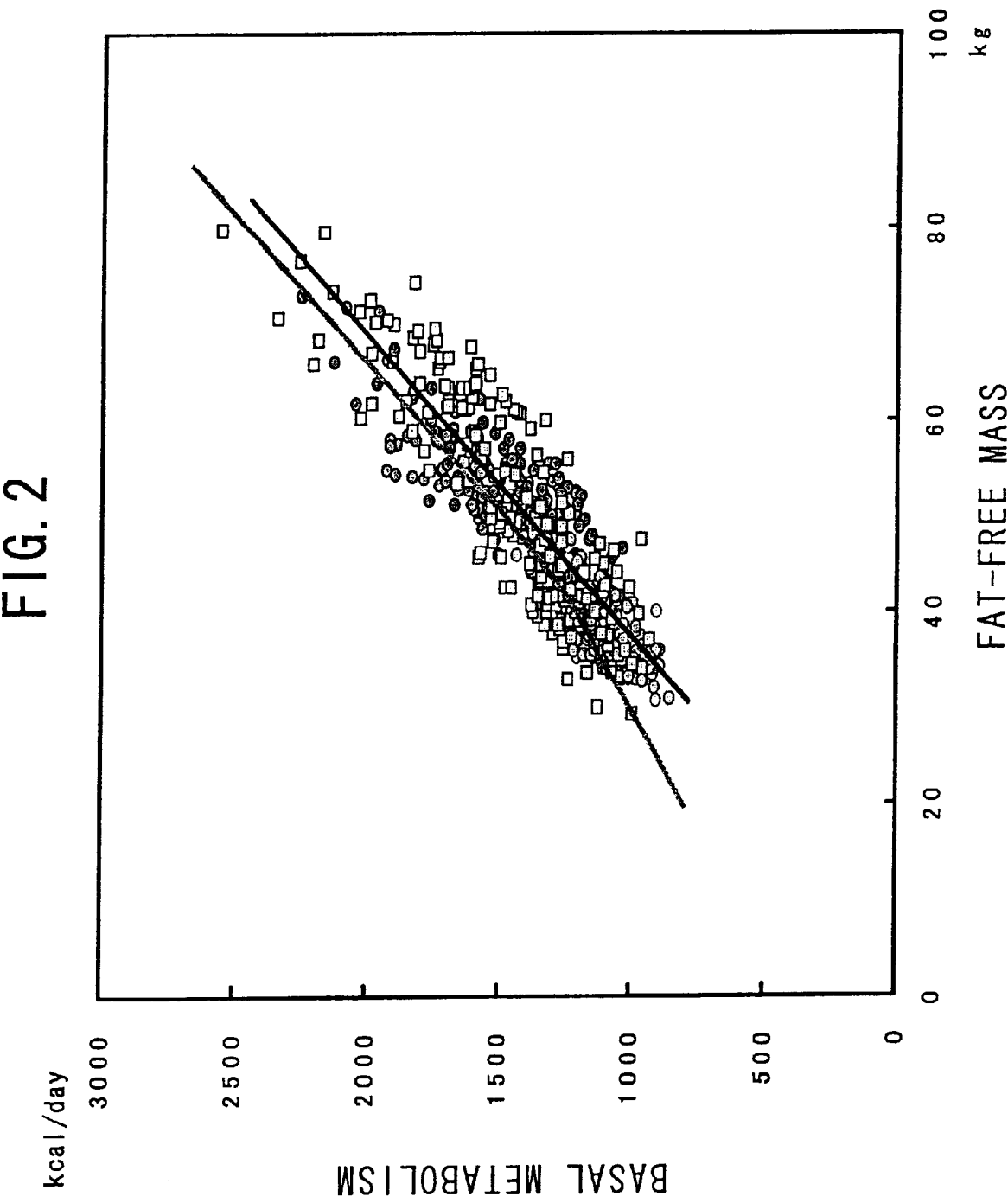
FIG. 2 is a graph showing a relationship between fat-free mass and basal metabolism.

As shown in FIG. 2, a calculated value of basal metabolism tends to be lower than an observed value in humans with extremely low fat-free mass. The inventors of the present invention have found that a reciprocal of an age and squared thereof in addition to fat-free mass is preferably utilized when calculating basal metabolism. Accordingly, the inventors have found that the basal metabolism can be calculated using the formula represented by BMR=A×FFM$^2$+B×FFM+C×(1/age)+D, in which BMR is basal metabolism (kcal/day), FFM is fat-free mass (kg), and A, B, C, and D are constants. It should be understood, however, that the formula is not limited to using metric measuring system values and can use any type of measuring system values.

Figure 7:
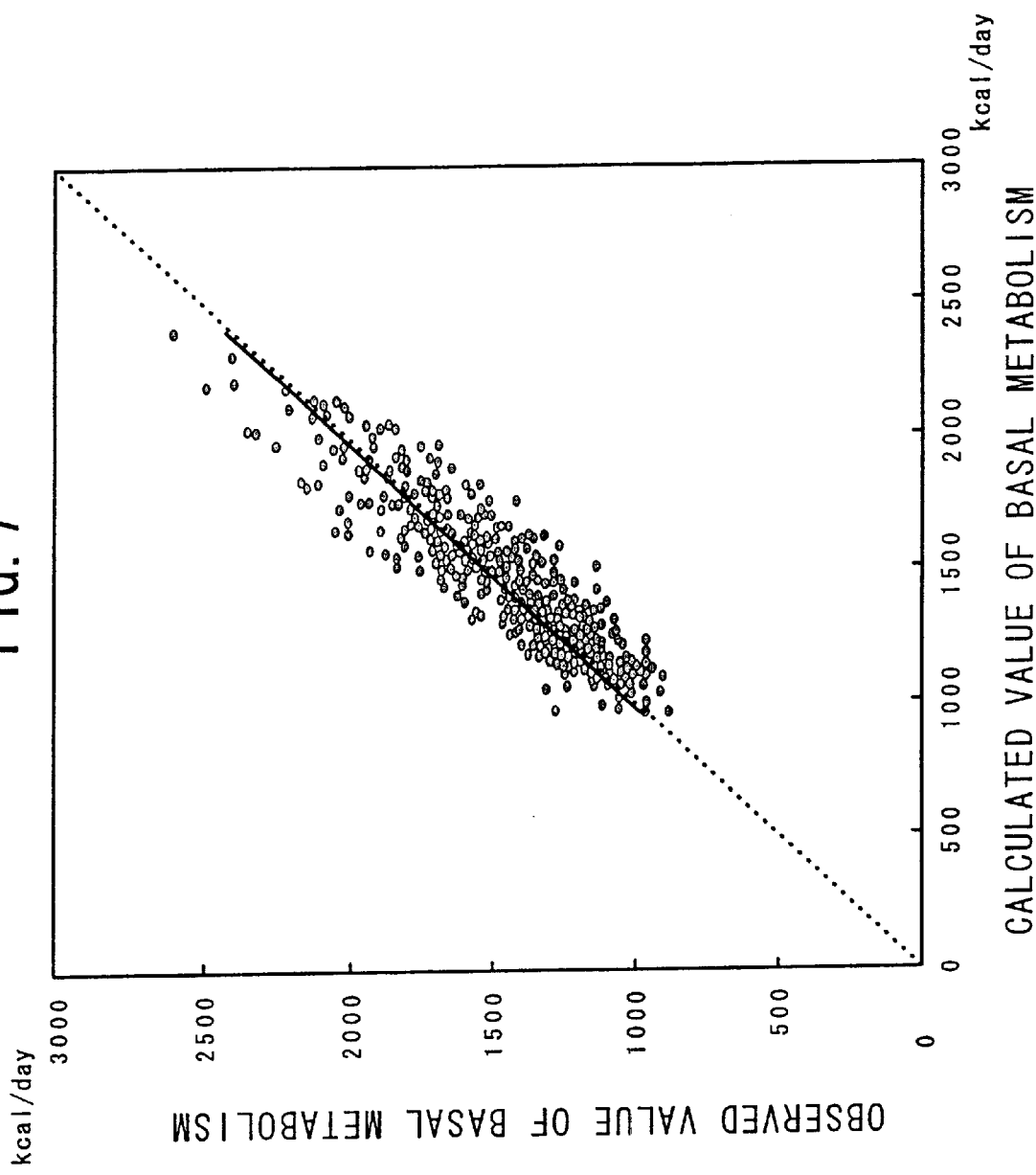
FIG. 7 is a graph showing a relationship between a calculated value of basal metabolism and an observed value of basal metabolism.
Figure 8:
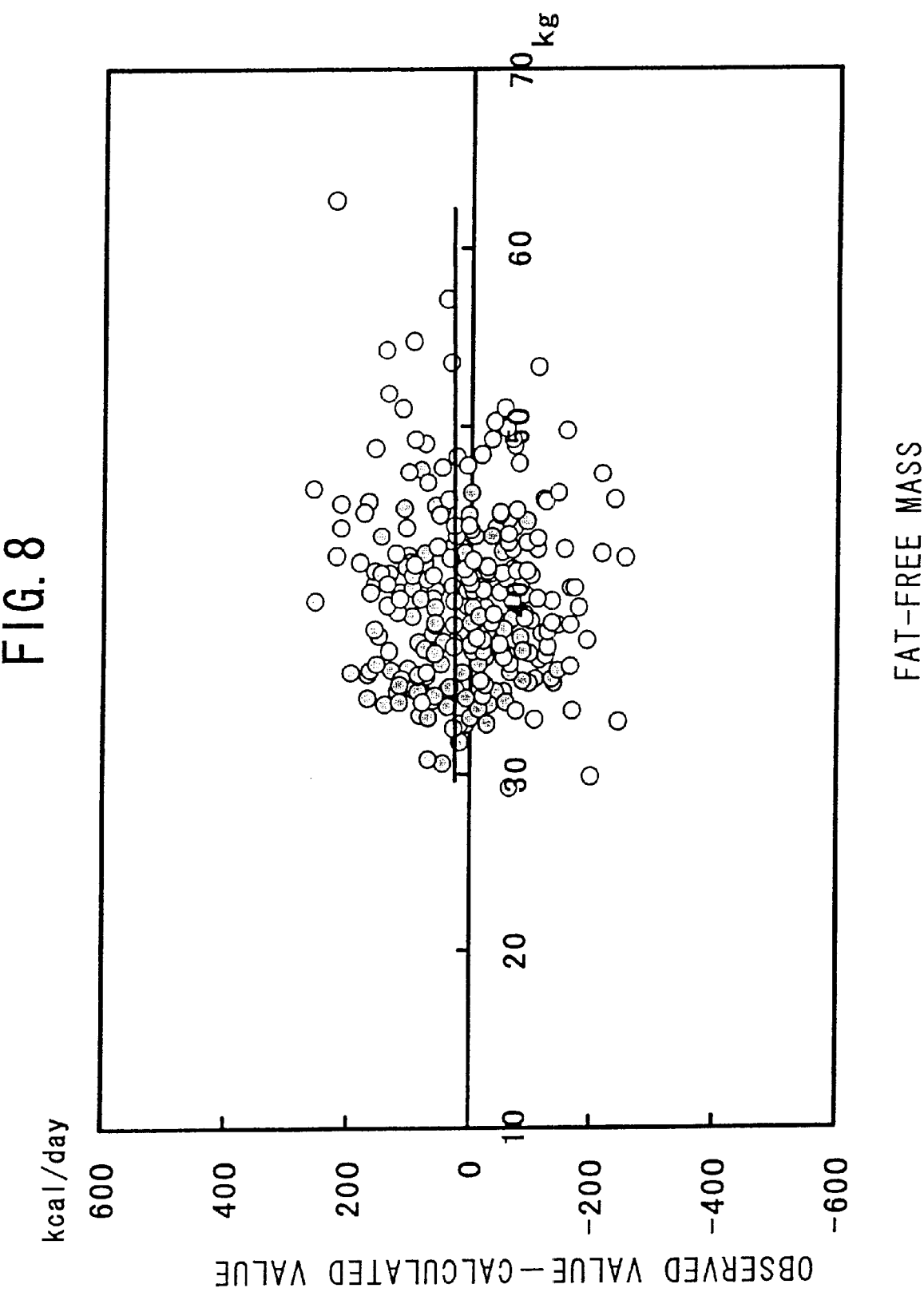
FIG. 8 is a graph showing a relationship between difference between an observed value of basal metabolism and a calculated value of basal metabolism and fat-free mass.

As shown in FIG. 7, a correlation coefficient between the basal metabolism obtained using the above mentioned formula and the observed basal metabolism is 0.88. The observed value was obtained by analysis of expired gas. As shown in FIG. 8, the difference between an observed value and a calculated value against fat-free mass is almost identical.

The inventors of the present invention recognize that the calculated value of basal metabolism tends to be lower than an observed value thereof in humans with low fat-free mass, especially in young slim female and in children. As such, the inventors of the present invention have found that a reciprocal of an age and body weight in addition to fat-free mass is preferably utilized to calculate basal metabolism. Accordingly, the inventors have found that the basal metabolism can be calculated using the formula represented by BMR=A×FFM+B×(1/age)+C×body weight+D, in which BMR is basal metabolism (kcal/day), FFM is fat-free mass (kg), and A, B, C, and D are constants. It should be understood, however, that the formula is not limited to using metric measuring system values and can use any type of measuring system values.

Figure 9:
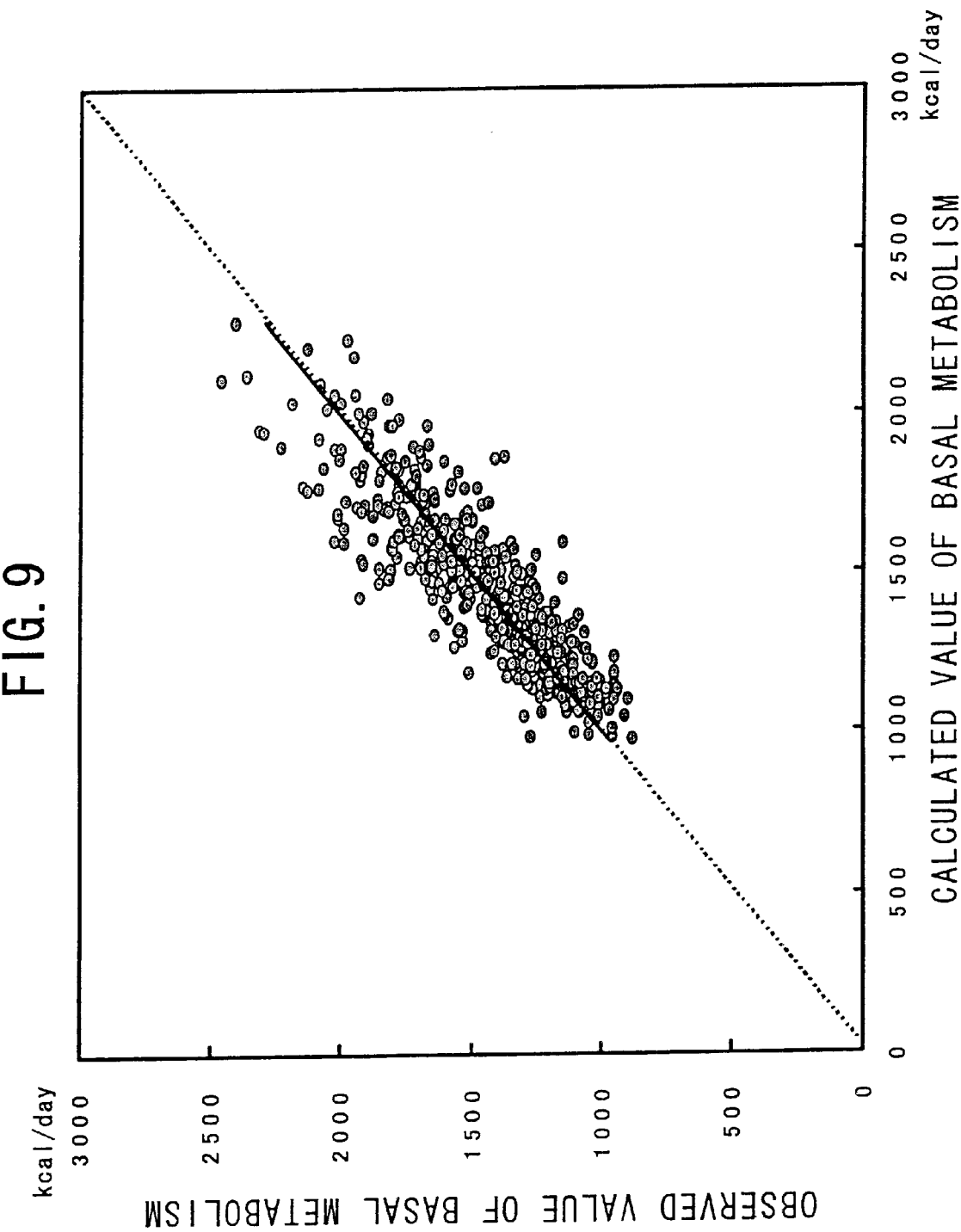
FIG. 9 is a graph showing a relationship between a calculated value of basal metabolism and an observed value of basal metabolism.

As shown in FIG. 9, a correlation coefficient between the basal metabolism obtained using the above mentioned formula and the observed basal metabolism is 0.879. The observed value was obtained by analysis of expired gas. The difference between an observed value and a calculated value against fat-free mass is half of the data shown in FIG. 6.

As shown in FIG. 2, a calculated value of basal metabolism tends to be lower than an observed value thereof in human with extremely low fat-free mass. The inventors of the present invention have found that a reciprocal of an age and squared thereof in addition to fat-free mass should be paid is preferably utilized to calculate basal metabolism. Accordingly, the inventors have found that the basal metabolism can be calculated using the formula represented by BMR=A×FFM$^2$+B×FFM+C×(1/age)+D×body weight+E, in which BMR is basal metabolism (kcal/day), FFM is fat-free mass (kg), and A, B, C, D, and E are constants. It should be understood, however, that the formula is not limited to using metric measuring system values and can use any type of measuring system values.

Figure 10:
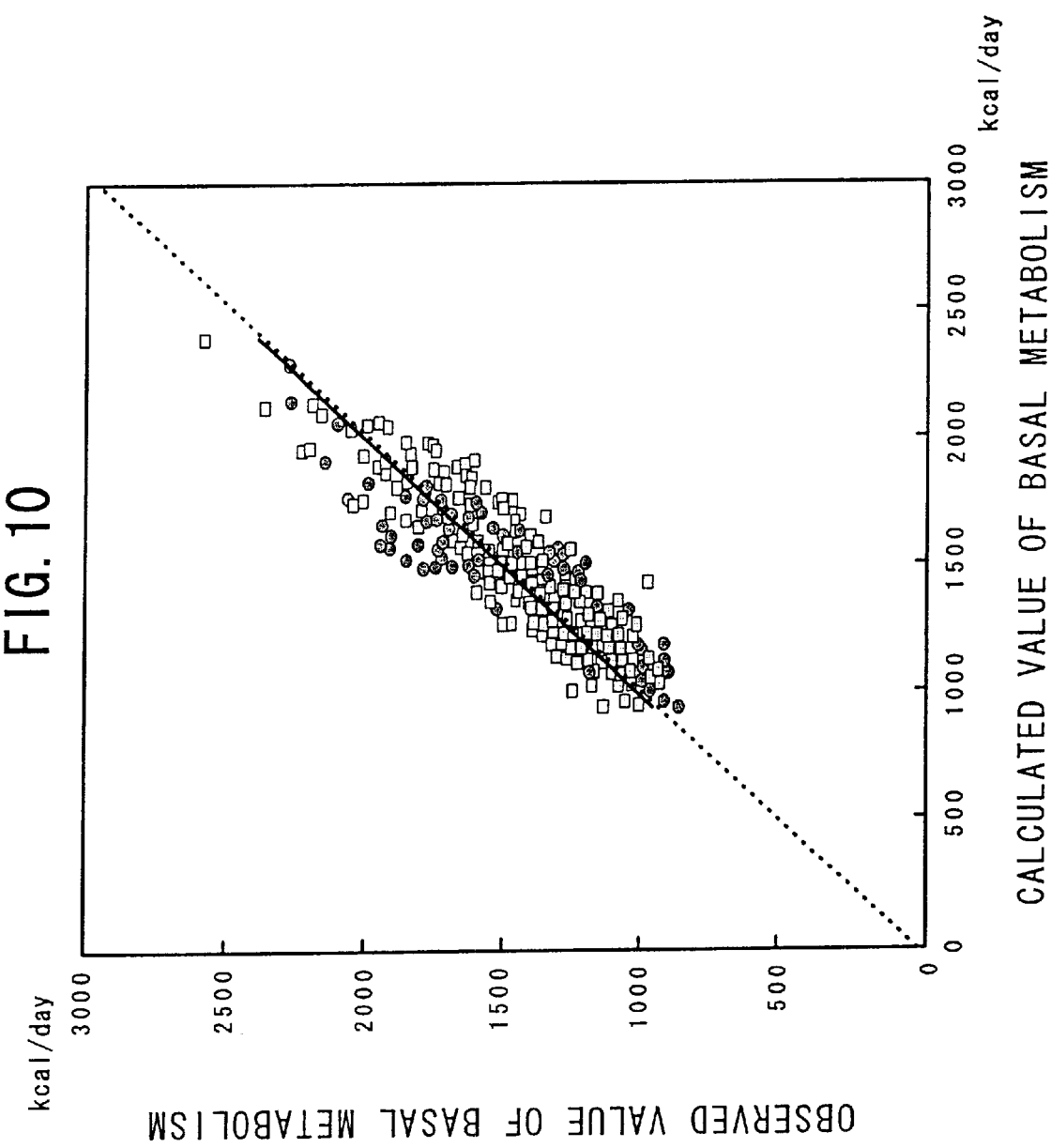
FIG. 10 is a graph showing a relationship between a calculated value of basal metabolism and an observed value of basal metabolism.

As shown in FIG. 10, a correlation coefficient between the basal metabolism obtained using the above mentioned formula and the observed basal metabolism is 0.88. The observed value was obtained by analysis of expired gas. The difference between an observed value and a calculated value against fat-free mass is substantially identical with the data shown in FIG. 8.

According to the above-described embodiment of the invention, values for fat-free mass, age, and body weight are required to calculate the basal metabolism. The basal metabolism can therefore be determined, for example, by changing a control program of a commercially available body fat measuring apparatus attached with weighing machine or an body fat measuring apparatus in which a value of body weight is manually inputted. Any method of determining fat-free mass is acceptable for use with the invention, for example, a bioimpedance analysis method (BIA method), a DEXA method, a method using a caliper, and the like may be employed.

Figure 11:
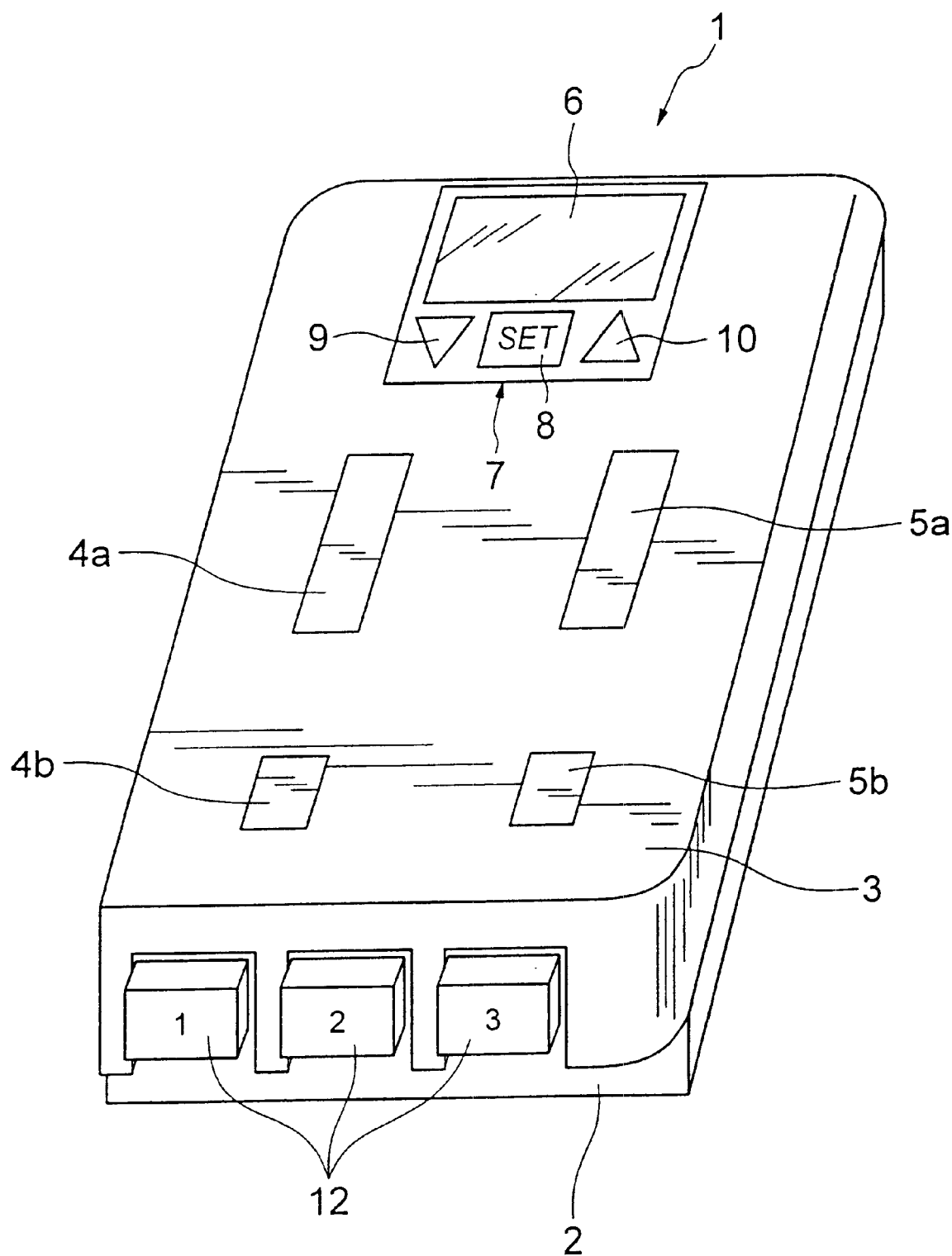
FIG. 11 is an external view of an apparatus for use in measuring basal metabolism in accordance with the present invention.

Referring to FIG. 11, an embodiment of the above described apparatus used for measuring basal metabolism will be described. As illustrated in FIG. 11, the apparatus is a combination of a body fat measuring assembly attached to a weighing machine and an apparatus for use in measuring basal metabolism. The equipment main body 1 comprises a base 2 and a platform 3. In operation, a subject mounts the platform 3, so that the body weight of the subject can be determined, although other methods of determining body weight can be employed as is well known in the art of measuring the weight of a body.

The platform 3 can include any device capable of measuring body fat. For example, electrodes, such as those used on a body fat measuring assembly, can be provided on the upper surface of the platform 3. Electrodes 4a and 5a are electrodes for current and are respectively for a left and right foot. Electrodes 4b and 5b are electrodes for measuring voltage and are respectively for the left and right foot.

The platform can also include a display portion 6 and an input portion 7 into which data about the subject can be inputted. In an aspect of the invention, the display portion 6 and input portion 7 are provided at a forward part of the upper surface of the platform 3. The input portion 7 can include a SET key 8 which determine data, a down key 9 which lowers a value of the data, an up key 10 which heightens a value of the data, and a personal key 12.

Personal keys 12 can be provided on the front of the base 2 of the above mentioned equipment main body 1. The keys 12 can be used to call up the personal data for each subject when a particular key 12 is pushed. Although three personal keys are illustrated in this embodiment, the invention is not limited in this manner and any number of keys may be used. For example, two keys or four keys can be provided. The detailed description of this construction is omitted because this construction is the same as a conventional body fat measuring assembly attached with a weighing machine.

Figure 12:
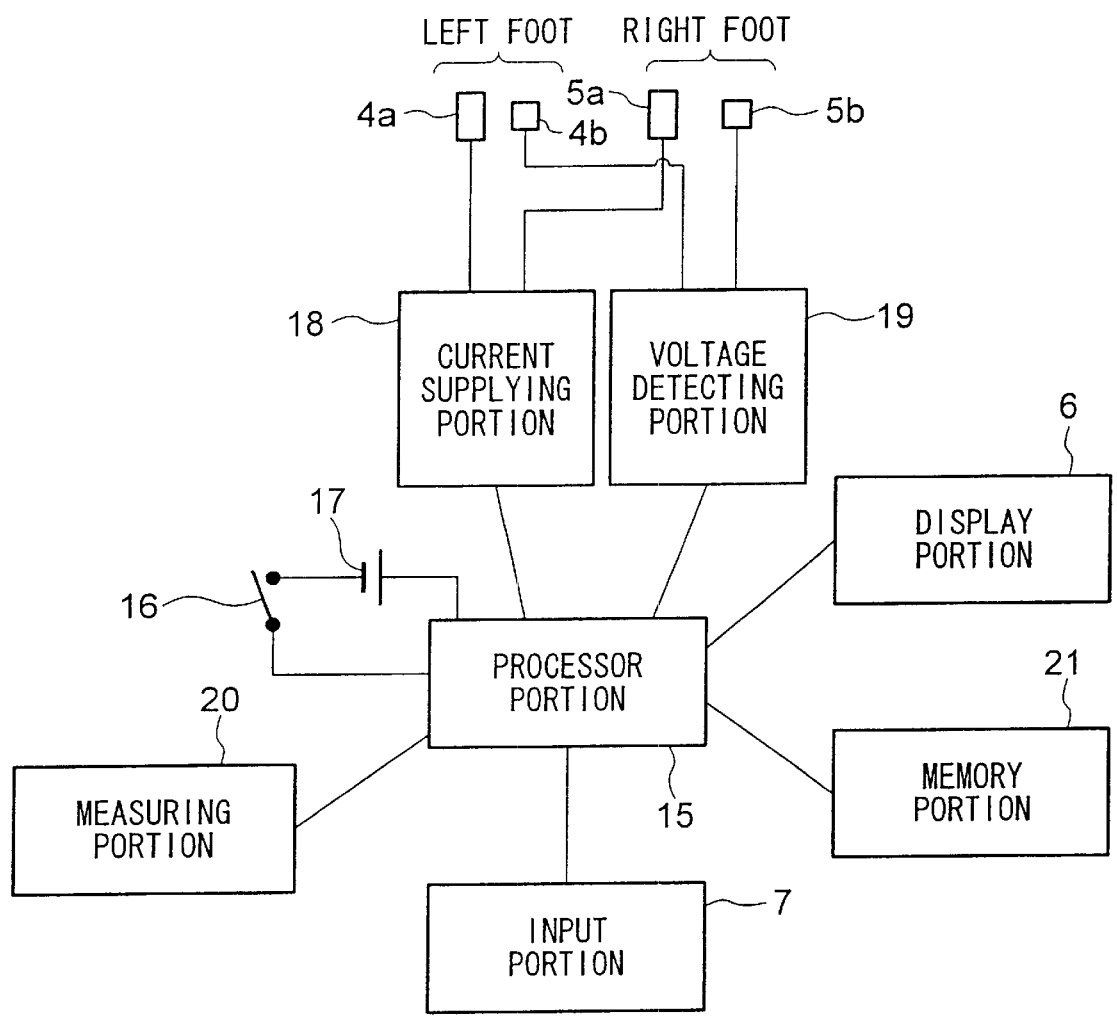
FIG. 12 is an electrical block diagram of an apparatus for use in measuring basal metabolism in accordance with the present invention.

FIG. 12 displays an electrical block diagram of the apparatus 1 shown in FIG. 11 for use in measuring basal metabolism. The reference numerals used in FIG. 12 represent the same features shown in FIG. 11. A processor portion 15, which process a variety of data, can be connected with a battery 17 through a power supplying switch 16. It should be noted that the processor portion 15 can be supplied with power via other sources of power, as is known in the art.

A high frequency current supplying portion 18 is connected with the processor portion 15, and the current supplying portion 18 is also connected with the electrodes 4a and 5a. Furthermore, a voltage detecting portion 19 is connected with the processor portion 15, and the voltage detecting portion 19 is also connected with the electrodes 4b and 5b. Still further, the processor portion 15 can be connected to a measuring portion 20 for determining body weight, an input portion 7, a display portion 6, and a memory portion 21 to memorize data for processing.

Figure 13:
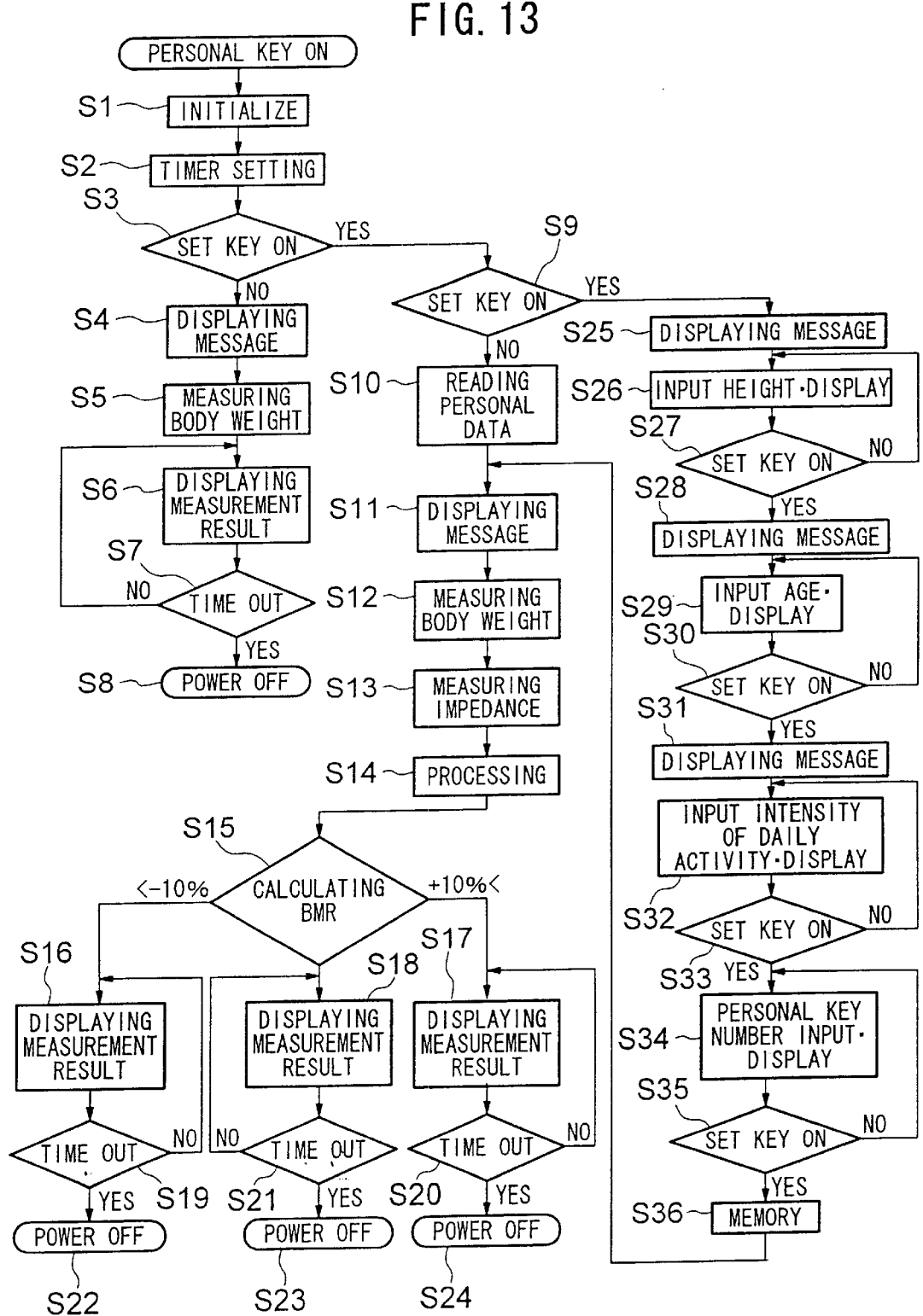
FIG. 13 is a flowchart of an apparatus for use in measuring basal metabolism in accordance with the present invention.
Figure 14:
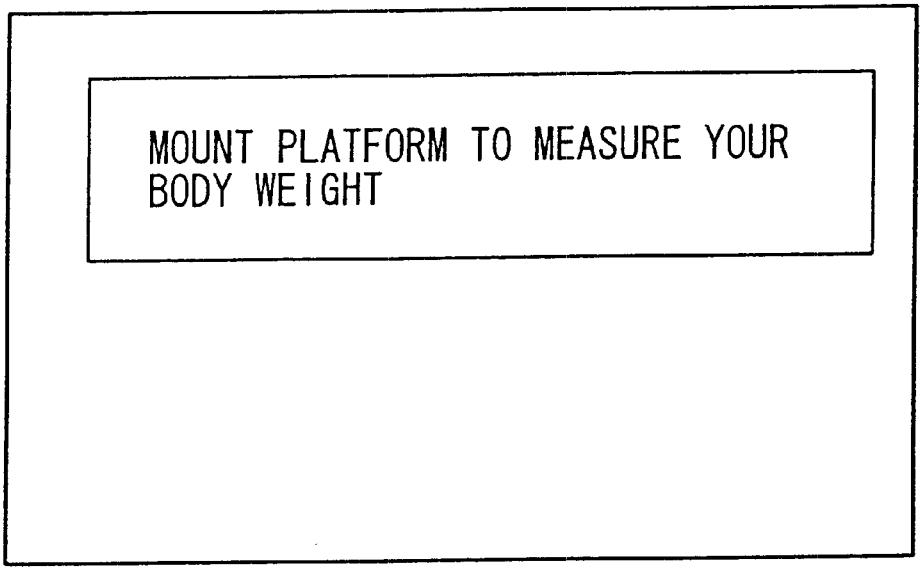

In an example of operation of the embodiment shown in FIGS. 11 and 12 will be described in conjunction with a flowchart shown in FIG. 13 and example of displays shown in FIGS. 14 to 22. Initially, the power supplying switch 16 or one of the personal keys 12 shown in FIG. 12 is turned on to initiate the supply of power. After power is supplied, the display portion 6 and the like are initialized in Step S1. Then, in Step S2, an auto power off timer (for example, 30 seconds) to turn off the power supplying switch can be set, so that a signal enters into Step S3. Whether the SET key 8 is turned on or not is determined in Step S3. When the SET key 8 is turned off, a typical body weight measuring mode works and a message can be displayed which asks the subject to mount the platform 3 to measure the body weight, which is Step S4 as shown in FIG. 14.

Figure 15:
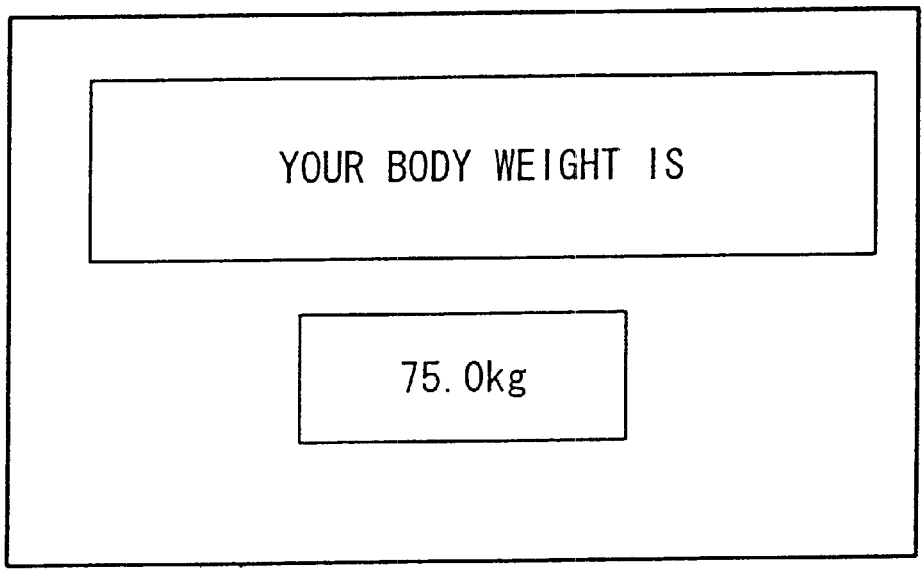

When the subject mounts the platform 3, the data with respect to the body weight is sent from the measuring portion 20 to the processor portion 15 as Step S5. This creates a message displayed on the display portion 6 in Step 6 as shown in FIG. 15. This display continues, until the auto power off timer becomes timed out in Step S7. When the auto power off timer becomes timed out, a power supplying switch is turned off in Step S8.

When the SET key 8 is turned on in Step S3, a signal enters into Step S9, so that a determination can be made as to whether SET key 8 is turned on or not. When the SET key 8 is not turned on, personal data such as height and age, which correspond to one of the personal keys 12 (from number 1 to 3) being turned on, is called from the memory portion 21 and this data can be displayed on the display portion 6 (Step S10). Next, the body weight is measured in Steps S11 and S12 in the same manner as Steps S4 and S5. Also, impedance is measured in Step S13. The detailed description is omitted, because the measurement of the impedance is performed in the same manner as in a conventional body fat measuring assembly.

Body fat rate and fat-free mass (FFM) are obtained from the impedance, body weight, and personal data in Step S14. Further, basal metabolism and total amount of consumption energy, in which the intensity of daily activity is taken into consideration, are obtained on the basis of the above-described arithmetic expressions. As there are a plurality of arithmetic expressions, the arithmetic expression can be properly selected according to the accuracy of a measuring apparatus, the cost, and the like.

In Step S15, the calculated value of basal metabolism per kg body weight is assessed to be either (a) lower at 10% or more than the value of basal metabolism per kg body weight by age indicated by Ministry of Health and Welfare (Step S16), (b) higher at 10% or more (Step S17), or (c) between the above-mentioned two groups (Step S18).

Figure 16:
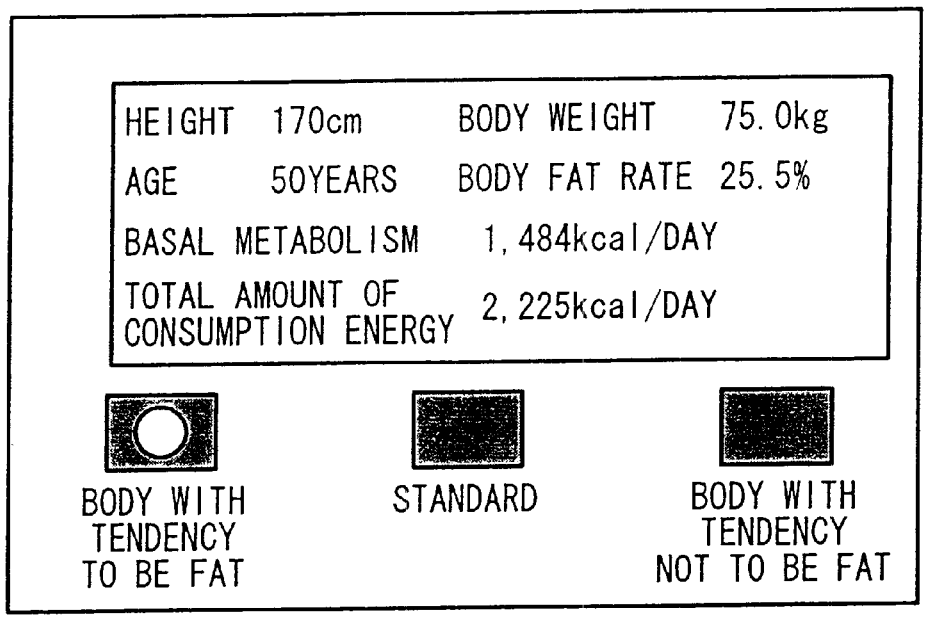

When the value is lower at 10% or more in Step S15, a mark is displayed at a part representing body with tendency to be fat among three patterns. These three patterns include a body with tendency to be fat, a standard body, and a body with tendency not to be fat. In Step S16, other information to be displayed include height, body weight, age, body fat rate, basal metabolism, and total amount of consumption energy as shown in FIG. 16.

At a value that is lower at 10% or more, the value of basal metabolism per kg body weight of a subject is lower than the value of basal metabolism indicated by Ministry of Health and Welfare. Thus, if an amount of consumption energy is low, such that when the subject uptakes the same calories from food as the other people do, a part of the calories are not metabolized and accumulate in the body. This results in accumulation of fat. The total amount of consumption energy is obtained by the basal metabolism in which the intensity of daily activity described below is taken into consideration.

Figure 17:
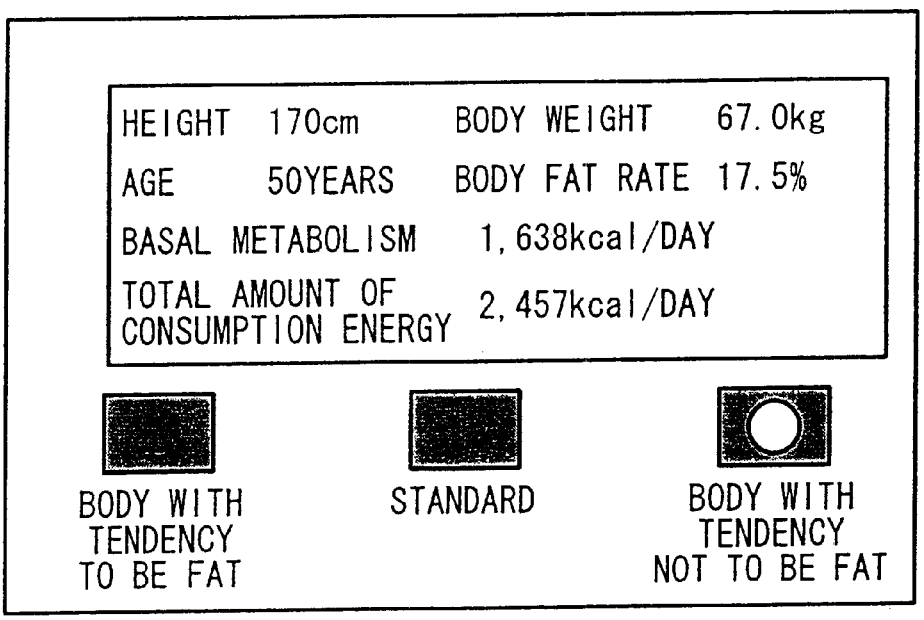

When, however, the basal metabolism calculated in Step S15 is higher at 10% or more, the subject is typically a person with strong muscles and has a high energy consumption. Thus, when the subject uptakes the same calories from the food as the other people do, much of the calories are consumed and do not accumulate in the body. This results in no fat gain or a loss of fat. At this time, a mark is displayed at a part representing a body with tendency not to be fat in Step S17 as shown in FIG. 17.

A subject whose basal metabolism calculated in Step S15 is between −10% and +10% of the value of basal metabolism indicated by Ministry of Health and Welfare is estimated to be standard. Thus, a mark is displayed at a part representing a standard body in Step S18, as shown in FIG. 18. This display continues, until the auto power off timer becomes timed out in Steps S19, S20, and S21. When the auto power off timer is timed out, the power supplying switch is turned off in Steps S22, S23, and S24.

The range of difference between the above-described reference value of basal metabolism and a calculated value of basal metabolism for assessment is illustrative only. Ranges such as ±15% and ±20% may be available. Additionally, the display is not limited to this three-step display and can be modified.

Next, when the SET key 8 is assessed to be turned on in Step S9, a signal enters Step S25, so that personal data input mode works. In an aspect of the invention, when the apparatus is initially obtained and used for the first time, the personal data input mode can be automatically initialized, so as to obtain personal data that was not previously inputted.

In Step S25, a message can be displayed that asks for input of height, and the initial value, for example 160 cm, is displayed as shown in FIG. 19. The height value can be set for the subject using the up key 10 and the down key 9 in Step S26. Then, the SET key 8 is pushed in Step S27, so that a signal enters into next Step S28. When the SET key 8 is not pushed, there is no proceeding to wait for the SET key 8 being turned on, because data is not inputted.

Figure 20:
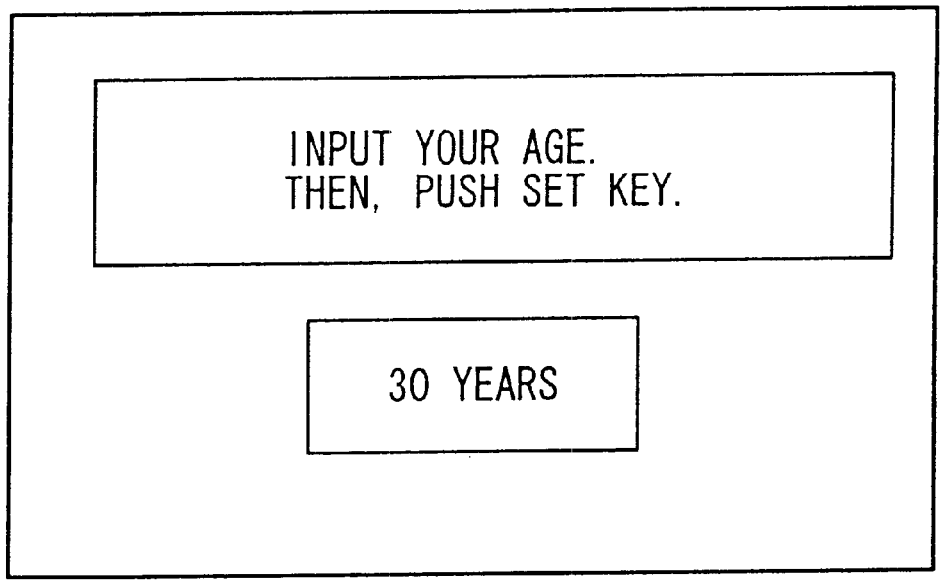

In Step S28, a message can be displayed that ask for input of age, and the initial value, for example 30 years, is displayed as shown in FIG. 20. In Steps S29 and S30, the process to input age can be the same as the process to input height.

Figure 21:
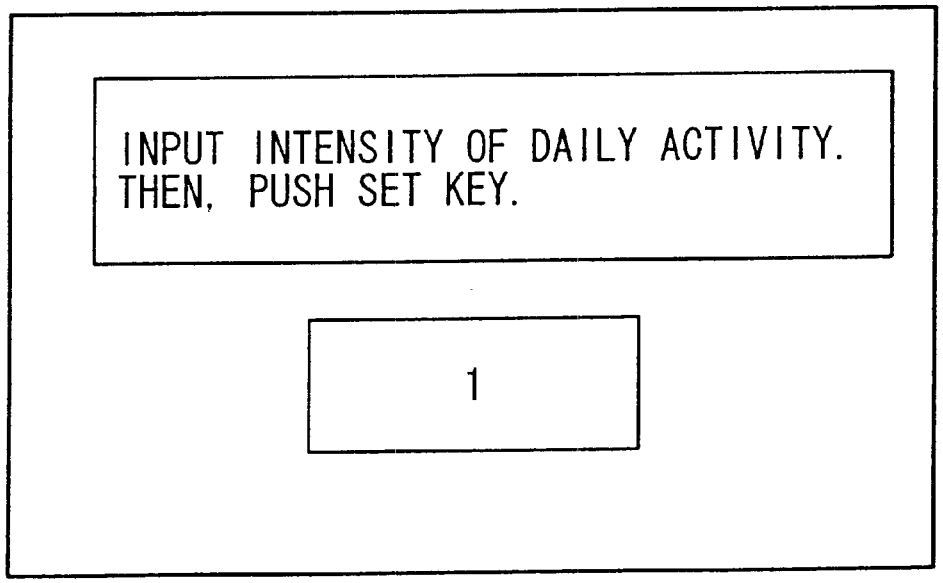
Figure 22:
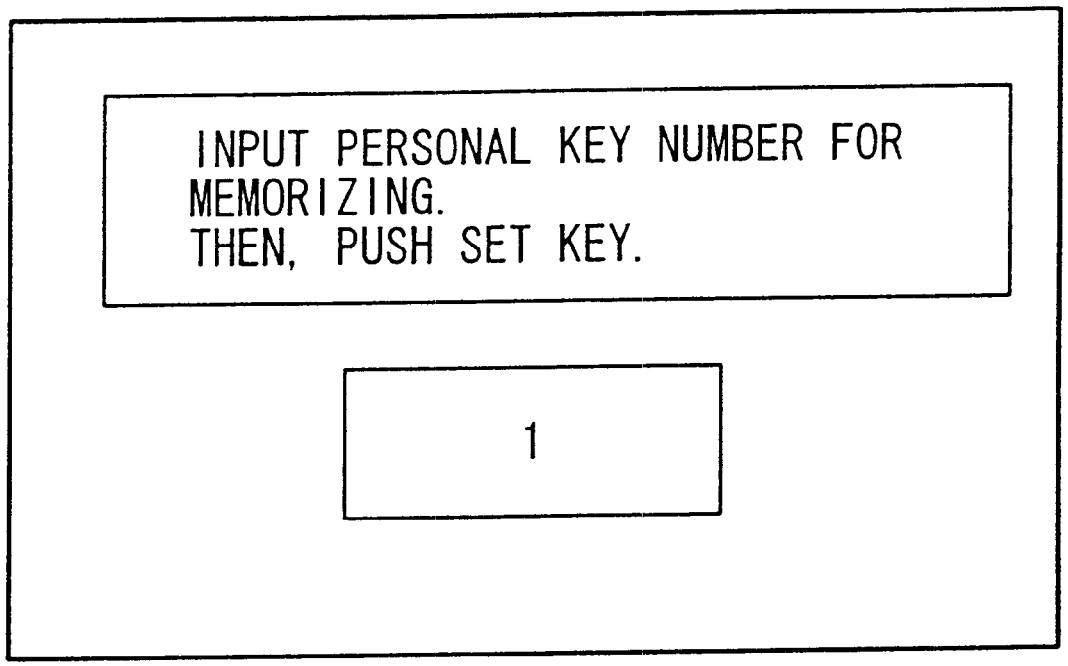

In another aspect of the invention, in Step 31 an intensity of a daily activity ranging from one to four, as indicated by Ministry of Health and Welfare, can be inputted, as shown in FIG. 21. The total amount of consumption energy per day in Step S14 is then calculated on the basis of the value of the intensity of daily activity. In Steps S32 and S33, the process to input intensity of daily activity can be the same as the process to input height.

In Steps S34 through S36, the above-described input data of the subject can be memorized through use of one of the personal keys 12 provided on the front of the equipment main body 1. The data is memorized in the memory portion 21 by inputting a number of the personal key 12. In Step S10, the personal data can then be displayed on the display portion 6 by pushing this number of personal key 12. After the memorization in Step S36 is completed, a signal is entered into the process before Step S11, which then can be used in the measuring mode. Although this input mode is described to enter into the measuring mode, the invention is not limited in this manner and the input mode is not required to enter into the measuring mode.

The present invention is carried out in the above-described form and includes advantages such as improving the accuracy of calculating of basal by utilizing the reciprocal of an age in addition to fat-free mass. In addition, the basal metabolism can be calculated using the formula represented by $BMR = A \times FFM + B \times (1/age) + C$, in which BMR is basal metabolism (kcal/day), FFM is fat-free mass (kg), and A, B, and C are constants, so that the value of the basal metabolism which corresponds with the observed value can be obtained. Furthermore, the basal metabolism can be calculated using the formula represented by $BMR = A \times FFM^2 + B \times FFM + C \times (1/age) + D$, in which BMR is basal metabolism (kcal/day), FFM is fat-free mass(kg), and A, B, C, and D are constants, so that the value of the basal metabolism which further corresponds with the observed value can be obtained.

The accuracy of calculating basal metabolism can be further improved by utilizing the reciprocal of an age and body weight in addition to fat-free mass. In addition, the basal metabolism can be calculated using the formula represented by $BMR = A \times FFM + B \times (1/age) + C \times body\ weight + D$, wherein BMR is basal metabolism (kcal/day), FFM is fat-free mass (kg), and A, B, C, and D are constants, so that the value of the basal metabolism which corresponds with the observed value can be obtained. Furthermore, the basal metabolism can be calculated using the formula represented by $BMR = A \times FFM^2 + B \times FFM + C \times (1/age) + D \times body\ weight + E$, wherein BMR is basal metabolism (kcal/day), FFM is fat-free mass (kg), and A, B, C, D, and E are constants, so that the value of the basal metabolism which further corresponds with the observed value can be obtained.

The present invention can be practiced by employing conventional methodology and equipment. Accordingly, the details of such equipment and methodology are not set forth herein in detail. In the previous descriptions, numerous specific details are set forth in order to provide a thorough understanding of the present invention. However, it should be recognized that the present invention can be practiced without resorting to the details specifically set forth. In other instances, well known processing structures or methods have not been described in detail, in order not to unnecessarily obscure the present invention.

Only the preferred embodiment of the present invention and but a few examples of its versatility are shown and described in the present disclosure. It is to be understood that the present invention is capable of use in various other combinations and environments and is capable of changes or modifications within the scope of the inventive concept as expressed herein.

What is claimed is:

1. An apparatus for measuring basal metabolism, comprising:
    an input device for receiving individual data, said individual data including an age of a subject;
    a measuring device for determining bioelectrical impedance of the subject;
    a fat-free mass calculation device for determining fat-free mass using said individual data from said input device and said impedance from said measuring device; and a basal metabolism calculation device for determining basal metabolism of the subject using said fat-free mass from said fat-free mass calculation device and a reciprocal of said age from said input device.

2. The invention according to claim 1, wherein the basal metabolism is calculated using a formula represented by BMR=A×FFM+B×(1/age)+C, wherein BMR is basal metabolism, FFM is fat-free mass, and A, B, and C are constants.

3. The invention according to claim 1, wherein the basal metabolism is calculated using a formula represented by BMR=A×FFM$^2$+B×FFM+C×(1/age)+D, wherein BMR is basal metabolism, FFM is fat-free mass, and A, B, C, and D are constants.

4. An apparatus for measuring basal metabolism, comprising:

an input device for receiving individual data, said individual data including an age and a body weight of a subject;

a measuring device for determining bioelectrical impedance of the subject;

a fat-free mass calculation device for determining fat-free mass using said impedance from said measuring device and a reciprocal of said individual data from said input device; and a basal metabolism calculation device for determining basal metabolism of the subject using said fat-free mass from said fat-free mass calculation device and said age and said body weight from said input device.

5. The invention according to claim 4, wherein the basal metabolism is calculated using a formula represented by BMR=A×FFM+B×(1/age)+C×body weight+D, wherein BMR is basal metabolism, FFM is fat-free mass, and A, B, C, and D are constants.

6. The invention according to claim 4, wherein the basal metabolism is calculated using a formula represented by BMR=A×FFM$^2$+B×FFM+C×(1/age)+D×body weight+E wherein BMR is basal metabolism, FFM is fat-free mass, and A, B, C, D, and E are constants.

7. The invention according to claim 4, wherein the body weight of the subject is manually inputted into said input device.

8. The invention according to claim 4, wherein the body weight of the subject is received into the input device as a signal from a body weight measuring device for determining the body weight of the subject.

9. The invention according to claim 4, wherein the body weight of the subject is received into the input device as a signal from a body weight measuring device for determining the body weight of the subject simultaneously when said impedance is determined.

* * * * *